United States Patent
Steiger et al.

(10) Patent No.: US 9,802,964 B2
(45) Date of Patent: Oct. 31, 2017

(54) PROCESS FOR PREPARING INDIUM ALKOXIDE COMPOUNDS, THE INDIUM ALKOXIDE COMPOUNDS PREPARABLE BY THE PROCESS AND THE USE THEREOF

(71) Applicants: Juergen Steiger, Taipei (TW); Duy Vu Pham, Oberhausen (DE); Anita Neumann, Recklinghausen (DE); Alexey Merkulov, Recklinghausen (DE); Arne Hoppe, Herne (DE); Dennis Fruehling, Marl (DE)

(72) Inventors: Juergen Steiger, Taipei (TW); Duy Vu Pham, Oberhausen (DE); Anita Neumann, Recklinghausen (DE); Alexey Merkulov, Recklinghausen (DE); Arne Hoppe, Herne (DE); Dennis Fruehling, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/900,936

(22) PCT Filed: May 15, 2014

(86) PCT No.: PCT/EP2014/059957
§ 371 (c)(1),
(2) Date: Dec. 22, 2015

(87) PCT Pub. No.: WO2014/206634
PCT Pub. Date: Dec. 31, 2014

(65) Prior Publication Data
US 2016/0159824 A1  Jun. 9, 2016

(30) Foreign Application Priority Data
Jun. 25, 2013 (DE) .......... 10 2013 212 017

(51) Int. Cl.
C07F 5/00 (2006.01)
C23C 18/12 (2006.01)
H01L 21/288 (2006.01)
C23C 18/14 (2006.01)

(52) U.S. Cl.
CPC ............. *C07F 5/003* (2013.01); *C07F 5/00* (2013.01); *C23C 18/1216* (2013.01); *C23C 18/1291* (2013.01); *H01L 21/288* (2013.01); *C23C 18/14* (2013.01)

(58) Field of Classification Search
CPC ........ C07F 5/00; C07F 5/003; C23C 18/1291; H01L 21/288
USPC ............................................. 556/1
See application file for complete search history.

(56) References Cited

U.S. PATENT DOCUMENTS

| | | | |
|---|---|---|---|
| 8,546,594 B2 | 10/2013 | Steiger et al. | |
| 8,580,989 B2 | 11/2013 | Steiger et al. | |
| 8,841,164 B2 | 9/2014 | Steiger et al. | |
| 8,859,332 B2 | 10/2014 | Steiger et al. | |
| 9,115,422 B2 | 8/2015 | Steiger et al. | |
| 9,194,046 B2 | 11/2015 | Hoppe et al. | |
| 9,293,326 B2 | 3/2016 | Steiger et al. | |
| 9,315,901 B2 | 4/2016 | Steiger et al. | |
| 2009/0112012 A1* | 4/2009 | Leedham | C07C 29/685 556/136 |
| 2012/0289728 A1* | 11/2012 | Steiger | C07F 5/003 556/1 |
| 2013/0104773 A1 | 5/2013 | Steiger et al. | |
| 2013/0116463 A1* | 5/2013 | Steiger | C07F 5/069 556/1 |
| 2016/0141177 A1 | 5/2016 | Steiger et al. | |

FOREIGN PATENT DOCUMENTS

DE  10 2010 031 592 A1  1/2012
WO  2011/072887 A1  6/2011

OTHER PUBLICATIONS

International Search Report dated Jul. 16, 2014, in PCT/EP2014/059957 Filed May 15, 2014.

* cited by examiner

*Primary Examiner* — Sudhakar Katakam
*Assistant Examiner* — Kofi Adzamli
(74) *Attorney, Agent, or Firm* — Oblon, McClelland, Maier & Neustadt, L.L.P.

(57) ABSTRACT

The present invention relates to indium alkoxide compounds preparable by reacting an indium trihalide $InX_3$ where X=F, Cl, Br, I with a secondary amine of the formula $R'_2NH$ where R'=alkyl, in a molar ratio of 8:1 to 20:1 in relation to the indium trihalide, in the presence of an alcohol of the generic formula ROH where R=alkyl, to a process for preparation thereof and to the use thereof for production of indium oxide-containing or (semi)conductive layers.

7 Claims, 1 Drawing Sheet

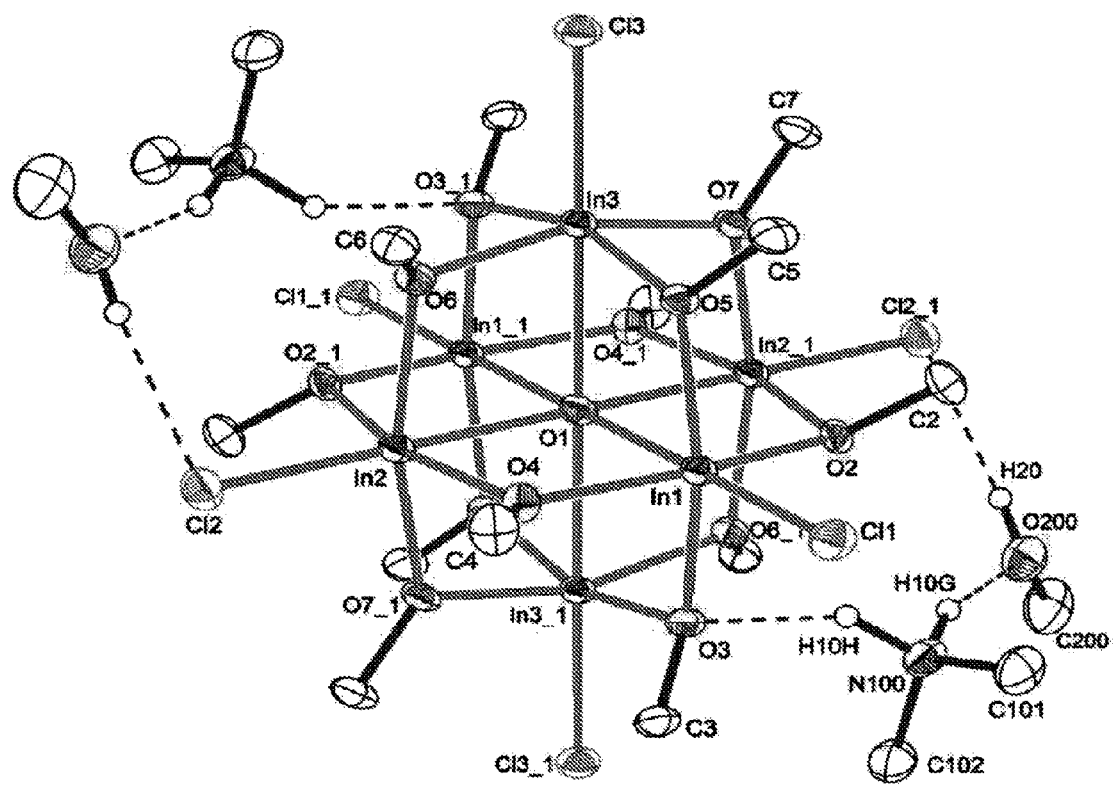

PROCESS FOR PREPARING INDIUM ALKOXIDE COMPOUNDS, THE INDIUM ALKOXIDE COMPOUNDS PREPARABLE BY THE PROCESS AND THE USE THEREOF

The present invention relates to processes for preparing indium alkoxide compounds, to the indium alkoxide compounds preparable by the process and to the use thereof.

The production of semiconductive electronic component layers by means of printing and other liquid deposition processes enables much lower production costs compared to many other methods, for example chemical vapour deposition (CVD), since the semiconductor can be deposited here in a continuous operation. Furthermore, in the case of relatively low process temperatures, it also becomes possible to work on flexible substrates, and possibly (particularly in the case of very thin layers and especially in the case of oxidic semiconductors) to achieve optical transparency of the printed layers. Semiconductive layers are understood here and hereinafter to mean layers which have charge carrier mobilities of 1 to 50 $cm^2/Vs$ for a component with a channel length of 20 μm at gate-source voltage 50 V and source-drain voltage 50 V.

Since the material of the component layer to be produced by means of printing methods crucially determines the particular layer properties, the selection thereof has an important influence on any component containing this component layer. Important parameters for printed semiconductor layers are the particular charge carrier mobilities thereof, and the processibilities and processing temperatures of the printable precursors used in the course of production thereof. The materials should have good charge carrier mobility and be producible from solution and at temperatures significantly below 500° C. in order to be suitable for a multitude of applications and substrates. Likewise desirable for many novel applications is optical transparency of the semiconductive layers obtained.

Because of the large band gap between 3.6 and 3.75 eV (measured for layers applied by vapour deposition, H. S. Kim, P. D. Byrne, A. Facchetti, T. J. Marks; *J. Am. Chem. Soc.* 2008, 130, 12580-12581), indium oxide (indium(III) oxide, $In_2O_3$) is a promising and therefore widely used semiconductor. Thin films of a few hundred nanometers in thickness may additionally have a high transparency in the visible spectral range of greater than 90% at 550 nm. In extremely highly ordered indium oxide single crystals, it is additionally possible to measure charge carrier mobilities of up to 160 $cm^2/Vs$. To date, however, it has not been possible to achieve such values by processing from solution (H. Nakazawa, Y. Ito, E. Matsumoto, K. Adachi, N. Aoki, Y. Ochiai; *J. Appl. Phys.* 2006, 100, 093706; and A. Gupta, H. Cao, Parekh, K. K. V. Rao, A. R. Raju, U. V. Waghmare; *J. Appl. Phys.* 2007, 101, 09N513).

Indium oxide is often used particularly together with tin(IV) oxide ($SnO_2$) as the semiconductive mixed oxide ITO. Because of the comparatively high conductivity of ITO layers with simultaneous transparency in the visible spectral region, one use thereof is that in liquid-crystal displays (LCDs), especially as "transparent electrode". These usually doped metal oxide layers are produced industrially particularly by costly vapour deposition methods under high vacuum. Owing to the great economic interest in ITO-coated substrates, there now exist some coating processes, based on sol-gel techniques in particular, for indium oxide-containing layers.

In principle, there are two options for the production of indium oxide semiconductors via printing methods: 1) particle concepts in which (nano)particles are present in printable dispersion and, after the printing operation, are converted to the desired semiconductor layer by sintering operations, and 2) precursor concepts in which at least one soluble or dispersible precursor, after the printing of an appropriate composition, is converted to an indium oxide-containing layer. The particle concept has two significant disadvantages compared to the use of precursors: firstly, the particle dispersions have colloidal instability which necessitates the use of dispersing additives (which are disadvantageous in respect of the later layer properties); secondly, many of the usable particles (for example because of passivation layers) only incompletely form layers by sintering, such that some particulate structures still occur in the layers. At the particle boundary thereof, there is considerable particle-particle resistance, which reduces the mobility of the charge carriers and increases the general layer resistance.

There are various precursors for the production of indium oxide layers. For example, in addition to indium salts, it is possible to use indium alkoxides (homoleptic compounds, i.e. those having only indium and alkoxide radicals) as precursors for the production of indium oxide-containing layers.

For example, Marks et al. describe components which have been produced using a precursor-containing composition comprising the salt $InCl_3$ and the base monoethanolamine (MEA) dissolved in methoxyethanol. After spin-coating of the composition, the corresponding indium oxide layer is obtained by a thermal treatment at 400° C. (H. S. Kim, P. D. Byrne, A. Facchetti, T. J. Marks; *J. Am. Chem. Soc.* 2008, 130, 12580-12581 and supplemental information).

WO 2011/072887 A1 describes a process for preparing indium(III) halogen dialkoxides and the use thereof for production of indium oxide-containing layers. Processes for production of indium oxide-containing layers from these indium(III) halogen dialkoxides are disclosed in WO 2011/073005 A2.

Indium(III) halogen dialkoxides, however, have to date not led to indium oxide-containing layers having sufficiently good electrical properties. Indium oxo alkoxides lead to better layer properties, for example the compounds of the generic formulae $In_6O_2X_6(OR)_6(R'CH(O)COOR'')_2(HOR)_x(HNR''')_2$, $In_7O_2(OH)(OR)_{12}X_4(ROH)_x$ and $M_xO_x(OR)_z[O(R'O)_eH]_aX_bY_c[R''OH]_d$ disclosed in WO 2012/010427 A1, WO 2012/010464 A1, and German application DE 10 2012 209918 which was yet to be published at the priority date of the present application.

In spite of the improvements already known, there is a constant need for improvements with regard to the layer formation properties and the properties of the layers obtained. More particularly, a suitable precursor should
  have good processibility, especially under air,
  be converted homogeneously to the oxide,
  be converted to the oxide at minimum temperatures and lead to layers having excellent electrical properties.

This complex profile of requirements is fulfilled by an indium alkoxide compound preparable by reacting
  an indium trihalide $InX_3$ where X=F, Cl, Br, I
  with a secondary amine of the formula $R'_2NH$ where R'=alkyl,
    in a molar ratio 8:1 to 20:1 in relation to the indium trihalide,
  in the presence of an alcohol of the generic formula ROH where R=alkyl.

Particularly good layers can be produced with indium alkoxide compounds where the secondary amine is used in the reaction in a molar ratio of 8:1 to 15:1, even better in a ratio of 8:1 to 12:1, in relation to the indium trihalide.

An indium alkoxide compound in the context of the present invention is understood to mean a compound having at least one indium atom and at least one alkoxide radical, which can be prepared via the described reaction of the trihalide with the secondary amine in the presence of an alcohol. The determination of the structure of these dissolved compounds obtainable by the process according to the invention is difficult. It is assumed, however, that the resulting compounds are halogenated indium oxo alkoxide compounds. Corresponding solid-state structures have been determined by X-ray structure analyses. It is assumed that similar structures for these compounds are also present in solution. Indium oxo alkoxides are indium clusters which may be present in ionic form and are bridged by oxo radicals, in which valences not coordinated by oxo radicals are at least partly coordinated by alkoxide radicals. For the indium alkoxide compounds obtainable by the process according to the invention, it is assumed that they are typically present in salt form after the synthesis, especially in the form of halogenated indium oxo alkoxide anions coordinated to cations.

A particularly preferred process product is an indium alkoxide compound of the generic formula $[In_6(O)(OR)_{12}X_6]^{2-} A_m^z (ROH)_x$ where R=alkyl, X=F, Cl, Br, I, A=cation, z=valency of the cation, m·z=2 and x=0 to 10, which can be prepared, inter alia, using secondary amines in a ratio of 9:1 to 10:1. The compound can be coordinated by alcohol molecules ROH and optionally also with other solvents present in the reaction.

Typical cations are ammonium ions $[NH_yR_{4-y}]^+$, preferably ammonium ions of the formula $[NH_2R_2]^+$.

A very particularly preferred compound is $[In_6(O)(OMe)_{12}Cl_6]^{2-}[NH_2R_2]^+_2(MeOH)_2$, which can be prepared by use of $InCl_3$, $Me_2NH$ (the latter in a ratio of 9:1 to 10:1) and MeOH (methanol). The structure thereof, determined via X-ray structure analysis, is shown in FIG. 1.

The present invention further provides a process for preparing indium alkoxide compounds, in which
an indium trihalide $InX_3$ where X=F, Cl, Br, I
is reacted with a secondary amine of the formula $R'_2NH$
where R'=alkyl,
in a molar ratio of 8:1 to 20:1 in relation to the indium trihalide,
in the presence of an alcohol of the generic formula ROH
where R=alkyl.

Indium trihalides of the formula $InX_3$ are known to those skilled in the art and can be purchased commercially.

Secondary amines of the formula $R'_2NH$ where R'=alkyl likewise form part of the prior art. Preferably, the alkyl radical R' is a linear, branched or cyclic $C_1$- to $C_{10}$-alkyl radical of the formula $C_nH_{2n+1}$ where n=1 to 10. Two R' radicals of one or two different secondary amines can also together form an alkylene radical $C_nH_{2n}$. Correspondingly usable compounds are, for example, dimethylamine, diethylamine, dipropylamine, pyrrolidine, piperidine and pyrrole. Preferred R' radicals are the methyl, ethyl, n-propyl and i-propyl radicals. Most preferably, the R' radical is methyl, since this leads to particularly good yields and particularly stable compounds.

The alcohols ROH used are preferably those having linear, branched or cyclic $C_1$- to $C_{10}$-alkyl radicals of the formula $C_nH_{2n+1}$ where n=1 to 10. Preferred R radicals here too are methyl, ethyl, n-propyl and i-propyl. Most preferably, the R radicals are methyl.

The indium trihalide is preferably used in proportions of 0.1 to 50% by weight, more preferably 1 to 25% by weight, most preferably 2 to 10% by weight, based on the total mass of all the components.

The indium trihalide can be dissolved, i.e. dissociated or complexed at the molecular level with solvent molecules/alcohol molecules, or dispersed in the liquid phase.

The alcohol ROH is used preferably in proportions of 50 to 99.9% by weight, more preferably 75 to 99% by weight, most preferably 80 to 96% by weight, based on the total mass of all the components.

The reaction mixture may further include at least one liquid solvent or dispersion medium which is inert in relation to the reaction, i.e. a solvent/dispersion medium or a mixture of various solvents/dispersion media which does/do not react with the indium trihalides under the reaction conditions. Usable with preference are aprotic solvents, especially those selected from the group of the aprotic nonpolar solvents, i.e. the alkanes, substituted alkanes, alkenes, alkynes, aromatics without or with aliphatic or aromatic substituents, halogenated hydrocarbons and tetramethylsilane, and the group of the aprotic polar solvents, i.e. of the ethers, aromatic ethers, substituted ethers, esters or acid anhydrides, ketones, tertiary amines, nitromethane, DMF (dimethylformamide), DMSO (dimethyl sulphoxide) or propylene carbonate.

If at least one such liquid solvent or dispersion medium inert in relation to the reaction is present in the reaction mixture, the proportion thereof is preferably 1 to 50% by weight, more preferably 1 to 25% by weight, most preferably 1 to 10% by weight, based on the total mass of all the components.

Preferably, the secondary amine is used in the reaction in a molar ratio of 8:1 to 15:1, even better in a ratio of 8:1 to 12:1, in relation to the indium trihalide, because indium alkoxide compounds of particularly good suitability for layer production can then be prepared in particularly high yield.

Preferably, the process according to the invention is performed by initially charging indium trihalide in alcohol ROH. The secondary amine is added in gaseous form, in liquid form, or dissolved in solvent (especially comprising ROH as solvent).

Preference is likewise given to addition under SATP conditions (25° C. and 1.013 bar).

Since the reaction can be controlled particularly efficiently in this way and leads to particularly good indium alkoxide compounds, the dialkylamine is preferably added at a rate of 0.5 to 5 mol per hour and mole of indium halide, preferably 1.15 to 2.60 mol per hour and mole of indium halide.

Further preferably, the reaction mixture is heated after addition of all the components. Preferably, the reaction mixture is heated to a temperature between 40 and 70° C. over a period of 1 to 10 h. Further preferably, the reaction mixture is heated to a temperature between 45 and 60° C. over a period of 1 to 5 h. Thereafter, the reaction mixture is cooled.

After the reaction has ended, the product or product mixture, which typically precipitates out, is preferably separated from the other constituents of the reaction composition. This is preferably done by filtration. Preferably, the separated product mixture is additionally dried and washed with suitable solvents.

Particularly good indium alkoxide compounds are the result when the product or product mixture obtained, after separation and optional drying and/or washing, is recrystallized. Preferably, the recrystallization is conducted in the alcohol ROH which was also used in the synthesis of the compound. Preferably, the recrystallization is conducted by dissolving the isolated product or product mixture in boiling alcohol and then recrystallization at temperatures of −30 to 0° C. The supernatant solvent is discarded and the crystalline product can be used further.

The inventive compound is particularly advantageously suitable for production of indium oxide-containing coatings having improved electrical properties, especially by means of wet-chemical processes. This improvement is surprising in that precursors of metal oxides are generally sought among the substances having a minimum crystallization tendency. Many of the inventive compounds, however, are cluster compounds which thus already have a microcrystallite structure. The desired metal oxide layer should also have more of an amorphous than a crystalline character, in order to have particularly good electrical properties. Contrary to expectation, it is possible with the inventive compound to produce particularly homogeneous layers.

Indium oxide-containing coatings in this case are understood to mean both indium oxide layers and layers essentially comprising indium oxide and further metals and/or metal oxides. An indium oxide layer in the context of the present invention is understood to mean a metallic layer producible from the indium alkoxides mentioned, having essentially indium atoms or ions, the indium atoms or ions being present essentially in oxidic form. Optionally, the indium oxide layer may also include halogen or alkoxide components from an incomplete conversion and/or nitrogen, hydrogen and/or carbon. The same also applies to layers essentially comprising indium oxide and further metals and/or metal oxides, with the proviso that these also include the further metals and/or metal oxides.

The inventive compound additionally has the surprising advantage that it can be used particularly efficiently for production of conductive or semiconductive indium oxide-containing layers for electronic components, especially for production of (thin-film) transistors, diodes or solar cells.

The examples which follow are intended to further illustrate the subject-matter of the present invention without having any limiting effect themselves.

INVENTIVE EXAMPLE

Synthesis

In a 30 l reactor freed of residual moisture, 1.30 kg of indium(III) chloride (InCl$_3$, 5.9 mol) are suspended in 17.38 kg of dried methanol and a protective gas atmosphere by stirring. Dimethylamine (2.57 kg, 57 mol) is metered in at room temperature by means of a mass flow controller (0.86 kg/h, about 4 h), in the course of which a slightly exothermic reaction can be observed. Thereafter, the reaction mixture is kept at a temperature of 50° C. for 2 h, cooled down to room temperature and filtered. The filter residue is washed with 4×500 ml of dried methanol and dried under reduced pressure (0.1 mbar) for 8 h. The material is dissolved in boiling methanol and crystallized at −20° C.

Production of a Formulation

The material obtained is dissolved at a concentration of 50 mg/ml in 1-methoxy-2-propanol. The concentrate obtained is formulated as follows: 1 part concentrate to 2 parts 1-methoxy-2-propanol to 1 part ethanol. A further 3% by weight of tetrahydrofurfuryl alcohol (THFA) is added to this formulation. All the solvents used are anhydrous (<200 ppm H$_2$O) and the mixing is effected under inert conditions (likewise anhydrous). The formulation obtained is finally filtered through a 200 nm PTFE filter.

Coating

A doped silicon substrate having an edge length of about 15 mm and having a silicon oxide coating thickness of about 200 nm and finger structures of ITO/gold was wetted with 100 μl of the abovementioned formulation. Then spin-coating is effected at 2000 rpm (30 seconds). Directly after this coating operation, the coated substrate is irradiated with UV radiation from a mercury vapour lamp within the wavelength range of 150-300 nm for 10 minutes. Subsequently, the substrate is heated on a hotplate at a temperature of 350° C. for one hour. After the conversion, it is possible to determine, in a glovebox, a value for field effect mobility (in the linear range) of μFET=14 cm$^2$/Vs at 2 VDS.

COMPARATIVE EXAMPLE

Synthesis

In a 500 ml glass round-bottom flask freed of residual moisture, 5.0 g of indium(III) chloride (InCl$_3$, 22.5 mmol) are dissolved under protective gas atmosphere in 250 ml of dried methanol by stirring, leaving a residue of InCl$_3$ of <10% by weight (based on the starting weight). The metered addition of the dimethylamine base (5.0 g, corresponding to 111 mmol) is controlled by means of a mass flow controller, and it is added in the stoichiometric amount based on InCl$_3$ at room temperature over a period of five hours, with observation of a slightly exothermic reaction at the start. Subsequently, the solution is evaporated completely, the remaining solid is taken up with 250 ml of dried methanol, filtered under protective gas (N$_2$), washed repeatedly (10 washes) with dried methanol and dried under reduced pressure (<10 mbar) at room temperature for 12 h. The product yield was >80 mol % of indium(III) chlordimethoxide.

Producing a Formulation

The material obtained is dissolved at a concentration of 50 mg/ml in 1-methoxy-2-propanol. The concentrate obtained is formulated as follows: 1 part concentrate to 2 parts 1-methoxy-2-propanol to 1 part ethanol. A further 3% by weight of tetrahydrofurfuryl alcohol (THFA) is added to this formulation. All the solvents used are anhydrous (<200 ppm H$_2$O) and the mixing is effected under inert conditions (likewise anhydrous). The formulation obtained is finally filtered through a 200 nm PTFE filter.

A doped silicon substrate having an edge length of about 15 mm and having a silicon oxide coating thickness of about 200 nm and finger structures of ITO/gold was wetted with 100 μl of the abovementioned formulation. Then spin-coating is effected at 2000 rpm (30 seconds). Directly after this coating operation, the coated substrate is irradiated with UV radiation from a mercury vapour lamp within the wavelength range of 150-300 nm for 10 minutes. Subsequently, the substrate is heated on a hotplate at a temperature of 350° C. for one hour. After the conversion, it is possible to determine, in a glovebox, a value for field effect mobility (in the linear range) of μFET=8 cm$^2$/Vs at 2 VDS.

The invention claimed is:

1. An indium alkoxide compound of formula

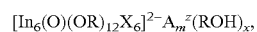

where R=alkyl; X=F, Cl, Br, and/or I; A=cation; z=valency of the cation; m·z=2; and x=0 to 10.

2. The compound according to claim 1, wherein the compound has formula [In$_6$(O)(OMe)$_{12}$Cl$_6$]$^{2-}$[NH$_2$R$_2$]$^+_2$(MeOH)$_2$.

3. A process for preparing an indium alkoxide compound, the process comprising: reacting
   an indium trihalide $InX_3$ where X=F, Cl, Br, and/or I
   with a secondary amine of formula $R'_2NH$ where R'=alkyl, in a molar ratio of 8:1 to 20:1 in relation to the indium trihalide,
   in the presence of an alcohol of formula ROH where R=alkyl,
   wherein the indium alkoxide compound is the indium alkoxide compound according to claim 1.

4. The process according to claim 3, wherein the molar ratio of the secondary amine to the indium trihalide is from 8:1 to 15:1.

5. The process according to claim 4, wherein
   the indium trihalide is initially charged in the alcohol ROH and
   the secondary amine is added in a gaseous form, in a liquid form, or dissolved in a solvent.

6. The process according to claim 5, wherein the secondary amine is added at a rate of 0.5 to 5 mol per hour and mole of $InX_3$.

7. The process according to claim 3, further comprising:
   separating and recrystallizing the indium alkoxide compound formed.

* * * * *